United States Patent [19]
Johnson

[11] Patent Number: 5,537,690
[45] Date of Patent: Jul. 23, 1996

[54] BODY SUPPORT GARMENT

[76] Inventor: Christina E. Johnson, 21914 Goldstone Rd., Topanga, Calif. 90290

[21] Appl. No.: 236,085

[22] Filed: May 2, 1994

[51] Int. Cl.$^6$ .................................. A41C 1/08; A61F 5/00
[52] U.S. Cl. ...................... 2/44; 2/45; 450/115; 450/116; 450/117; 450/122; 450/155; 602/19
[58] Field of Search .............................. 2/67, 44, 45, 92, 2/73; 450/2, 3, 4, 5, 6, 7, 8, 9, 10, 11, 12, 13, 14, 15, 16, 17, 18, 19, 20, 21, 22, 23, 24, 25, 26, 27, 113, 114, 115, 116, 117, 118, 119, 120, 121, 122, 123, 124, 125, 126, 127, 128, 129, 130, 131, 132, 155; 602/19

[56] References Cited

U.S. PATENT DOCUMENTS

| | | | |
|---|---|---|---|
| 198,348 | 12/1877 | Chapman | 450/86 |
| 604,298 | 5/1898 | Caroli . | |
| 1,170,282 | 2/1916 | Kops | 450/123 |
| 1,203,020 | 10/1916 | Leopold et al. | 450/121 |
| 1,636,459 | 7/1927 | Chappel . | |
| 1,753,739 | 4/1930 | Burns | 450/143 |
| 1,755,641 | 4/1930 | Foulke . | |
| 2,048,531 | 7/1936 | Yerkes | 450/6 |
| 2,088,423 | 7/1937 | Kispert | 450/15 |
| 2,115,398 | 4/1938 | Rosenthal | 450/86 X |
| 2,341,882 | 2/1944 | Scriggens | 450/130 X |
| 2,596,765 | 5/1952 | Dubner . | |
| 2,603,787 | 7/1952 | Leventhal | 450/130 X |
| 2,733,444 | 2/1956 | Goldstein | 450/130 |
| 3,099,266 | 7/1963 | Spitzer | 450/117 |
| 3,115,880 | 12/1963 | Blair | 450/143 |
| 3,282,264 | 11/1966 | Connelly . | |
| 3,441,027 | 4/1969 | Lehman . | |
| 3,603,316 | 9/1971 | Lehman . | |
| 3,812,862 | 5/1974 | Bernstein . | |
| 3,945,041 | 3/1976 | Rhee . | |
| 4,398,538 | 8/1983 | Johnson . | |
| 4,681,113 | 7/1987 | Coplans . | |
| 5,111,806 | 5/1992 | Travis . | |
| 5,205,815 | 4/1993 | Saunders . | |
| 5,221,227 | 6/1993 | Michels | 450/21 X |

Primary Examiner—Jeanette E. Chapman
Attorney, Agent, or Firm—William W. Haefliger

[57] ABSTRACT

A torso-shape controlling, lower back supporting garment comprising a garment having control fabric panel portions adapted to extend in waist shape controlling relation to torso front, back and sides; the control fabric panel portions include zones positioned to provide rigidity at the torso front and back and to yieldably resiliently stretch generally horizontally at the torso sides, whereby support is provided at the lower back, and an hourglass torso shape at the waist is produced. Convexly curved stays are located to transfer tensioning loading to at least two of the generally rigid zones of the panel portions.

15 Claims, 5 Drawing Sheets

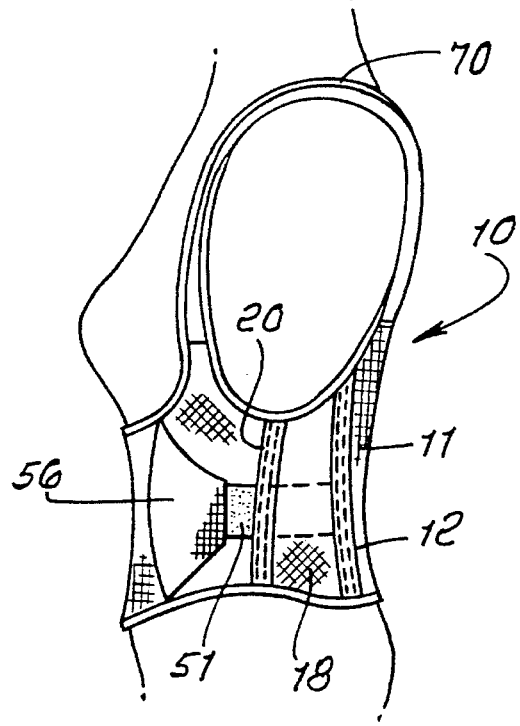
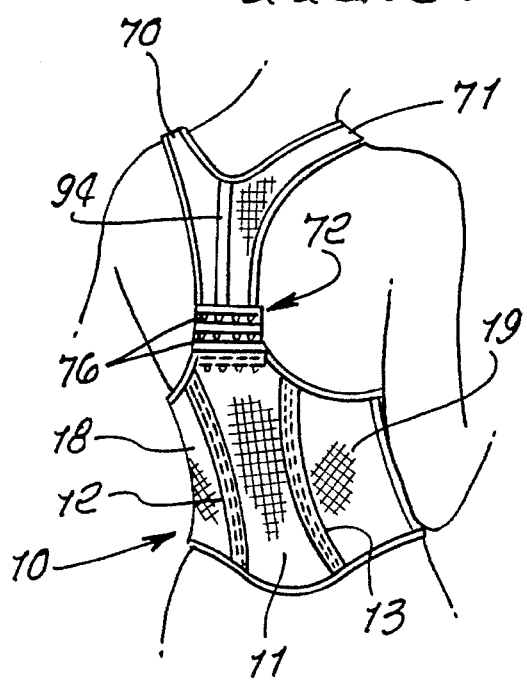
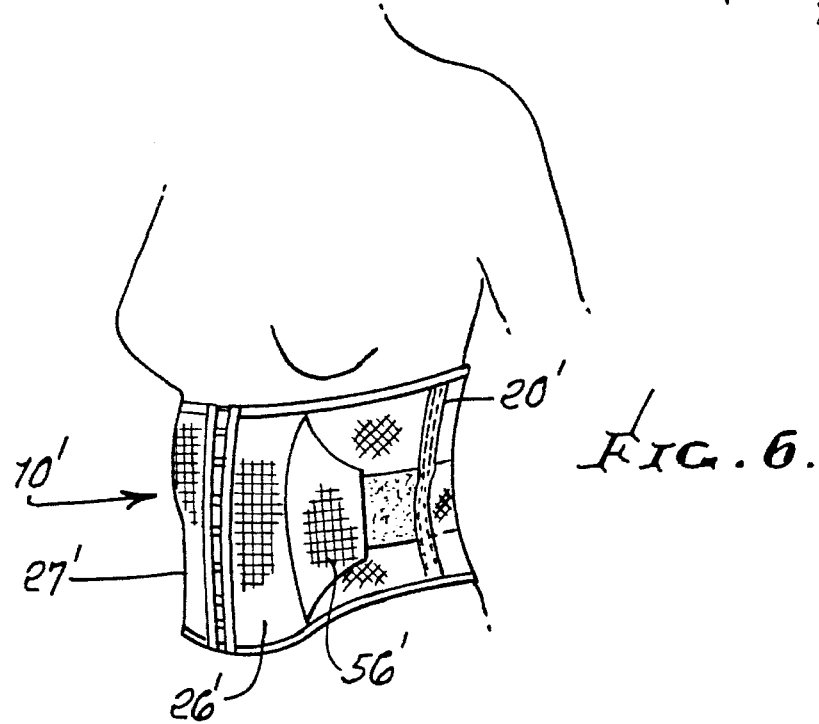

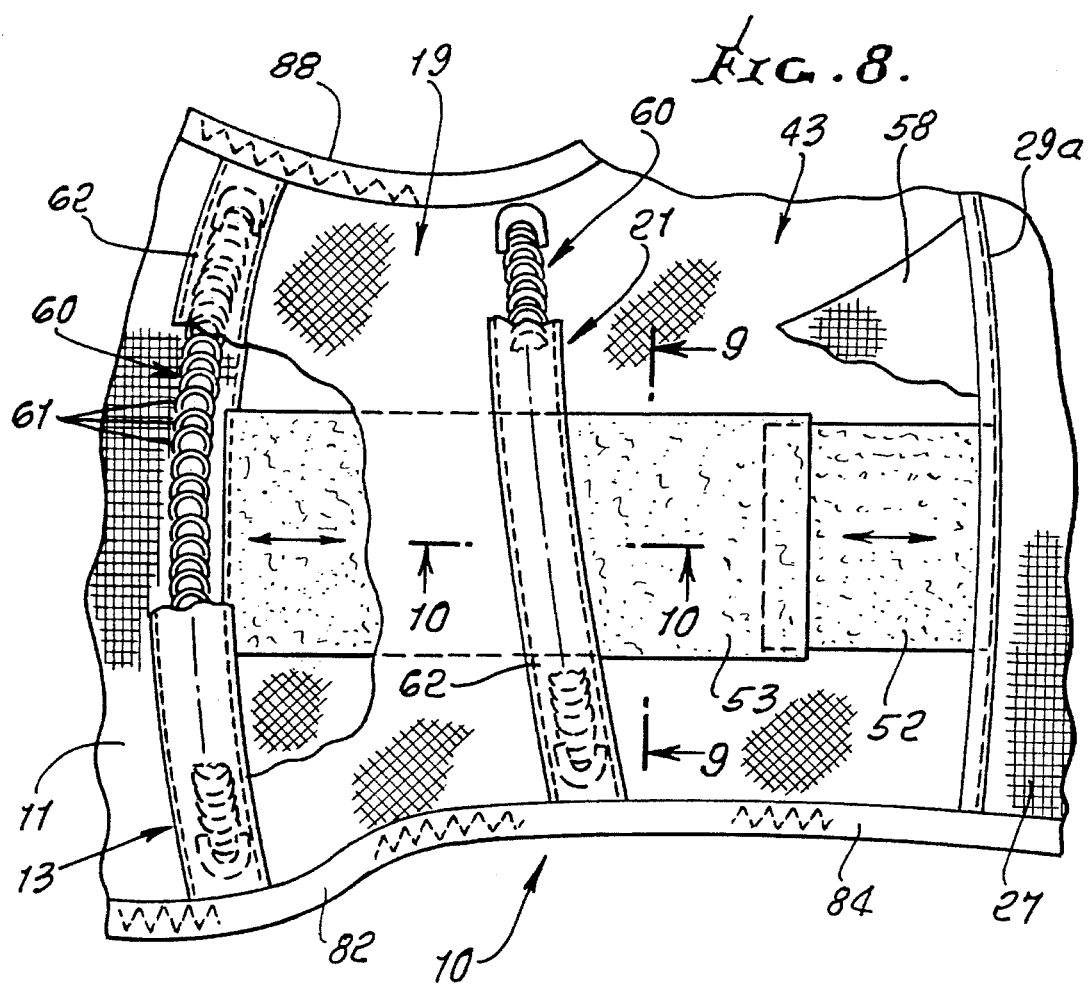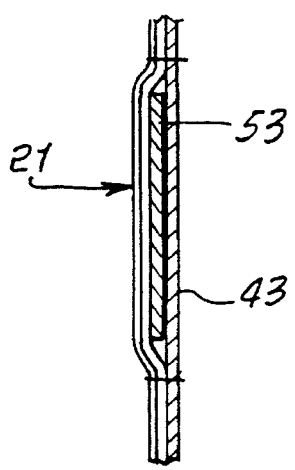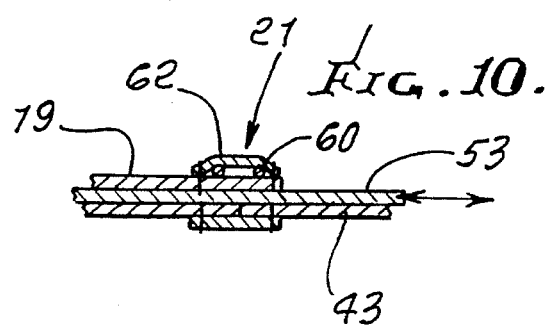

1

BODY SUPPORT GARMENT

BACKGROUND OF THE INVENTION

This invention relates generally to human torso control, as at the waist region, and more particularly, to an improved garment that provides support and protection to the lumbar region of the back, as well as maintaining an "hourglass" shape of the female torso at the waist.

There is need for an effective, comfortable support garment that conforms to the contours of a woman, achieves or enhances an "hourglass" look or shape of the female torso, and that creates control or compression at the front ("tummy" region) and also at the back (lower lumbar region). Adjustability of such a garment is also needed.

SUMMARY OF THE INVENTION

It is a major object of the invention to provide an improved garment meeting the above needs. Basically, the torso-shape controlling, lower back supporting garment comprises, in combination:

a) the garment having control fabric panel portions adapted to extend in waist shape controlling relation to torso front, back and sides, b) the control fabric panel portions including zones positioned to be generally rigid at the torso front and back, and to yieldably resiliently stretch generally horizontally at the torso sides, whereby an hourglass torso shape at the waist is produced, and whereby support is provided at the lower back. The generally rigid panel zones may be vertically stretchable, yieldably resiliently, but not horizontally, stretchable.

As will be seen, the achieved hourglass shape prevents "ride-up" of the garment.

Another object is to provide generally vertically extending stays incorporated in the garment at generally horizontally spaced locations between which at least two of the generally rigid panel portions are located, the stays having convex curvature to transfer tensioning loading to the two panel portions. In this regard, pairs of such stays are desirably incorporated in the garment, so that stays of one pair are at generally horizontally spaced locations between which one of the generally rigid panel portions is located; and so that stays of another pair are at generally horizontally spaced locations between which another of the generally rigid panel portions is located. The stays of each pair may be configured to have concave curvature toward the panel portions located therebetween, there being adjustable means for exerting tension loading on the stays. Also, the stays preferably are resiliently flexible and metallic, extending in a spiral loop pattern.

A further object is to provide straps or flaps associated with at least one of the panel portions that stretch horizontally, the straps having adjustable interconnection to permit controllable tightening of the garment about the torso waist. Pairs of such straps may be provided, at opposite sides of the garment, the straps anchored at stay regions; and a protective overlay strap may be provided to extend over the adjustable straps.

A further object is to provide a garment that will comfortably align the body or torso, while providing rigid, firm support at the back (waist level) and front, allowing garment stretching at the torso sides, all in such manner as to lessen likelihood of lower back injury and as to maintain good posture.

Yet another object is to provide garment shoulder straps that adjustably connect to the rear panel, or to side panels of the garment, to permit vertical adjustment of the shoulder straps relative to the garment.

These and other objects and advantages of the invention, as well as the details of an illustrative embodiment, will be more fully understood from the following specification and drawings, in which:

DRAWING DESCRIPTION

FIG. 4 is a left side elevation showing the FIG. 1 garment;

FIG. 5 is a rear elevational view of the FIG. 1 garment;

FIG. 6 is a view like FIG. 3 but showing a modified garment;

FIG. 8 is a fragmentary and enlarged view of a rear, right side portion of the FIG. 1 garment, as also seen in FIG. 7;

FIG. 9 is an enlarged, fragmentary sectional view taken on lines 9—9 of FIG. 8;

FIG. 10 is an enlarged, fragmentary sectional view taken on lines 10—10 of FIG. 8;

DETAILED DESCRIPTION

Figure 1:
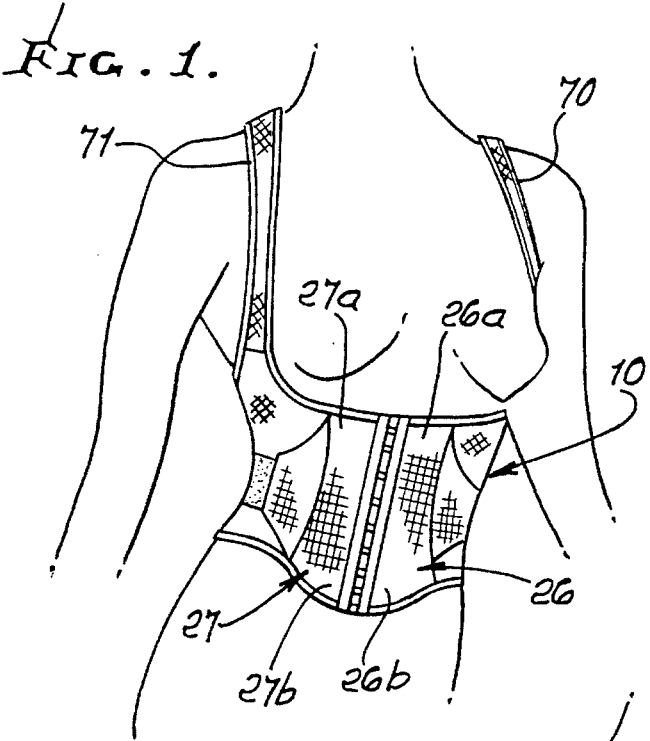
FIG. 1 is a frontal, partly perspective, elevational view showing a torso-shape controlling garment embodying the invention.
Figure 2:
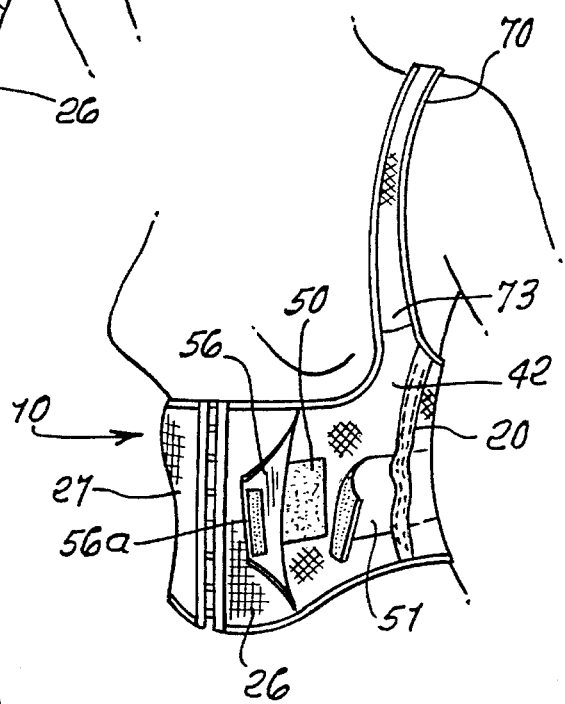
FIG. 2 is another frontal, partly perspective, elevational view showing side adjustment at the left-front side of the garment.
Figure 3:
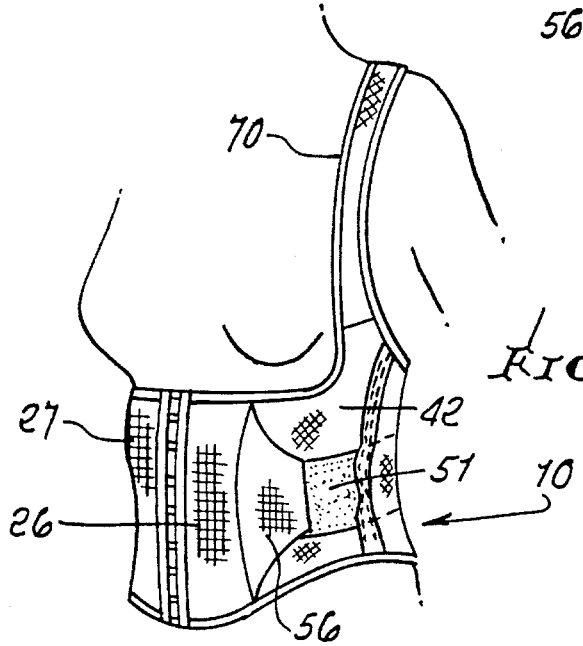
FIG. 3 is a view like FIG. 2 but showing completed side adjustment.

Basically, the garment shown in the drawings is characterized as having control fabric portions adapted to extend in waist-shape controlling, lower back supporting relation. The garment is also characterized as having control fabric panel portions adapted to extend in waist shape controlling relation to torso front, back and sides, whereby an hourglass torso shape at the waist is produced. Further, the garment is characterized in that the control fabric panel portions include zones positioned to be generally rigid at the torso front and back, and to yieldably resiliently stretch generally horizontally at the torso sides, whereby support is provided at the lower back, and the hourglass shape is produced.

Figure 7:
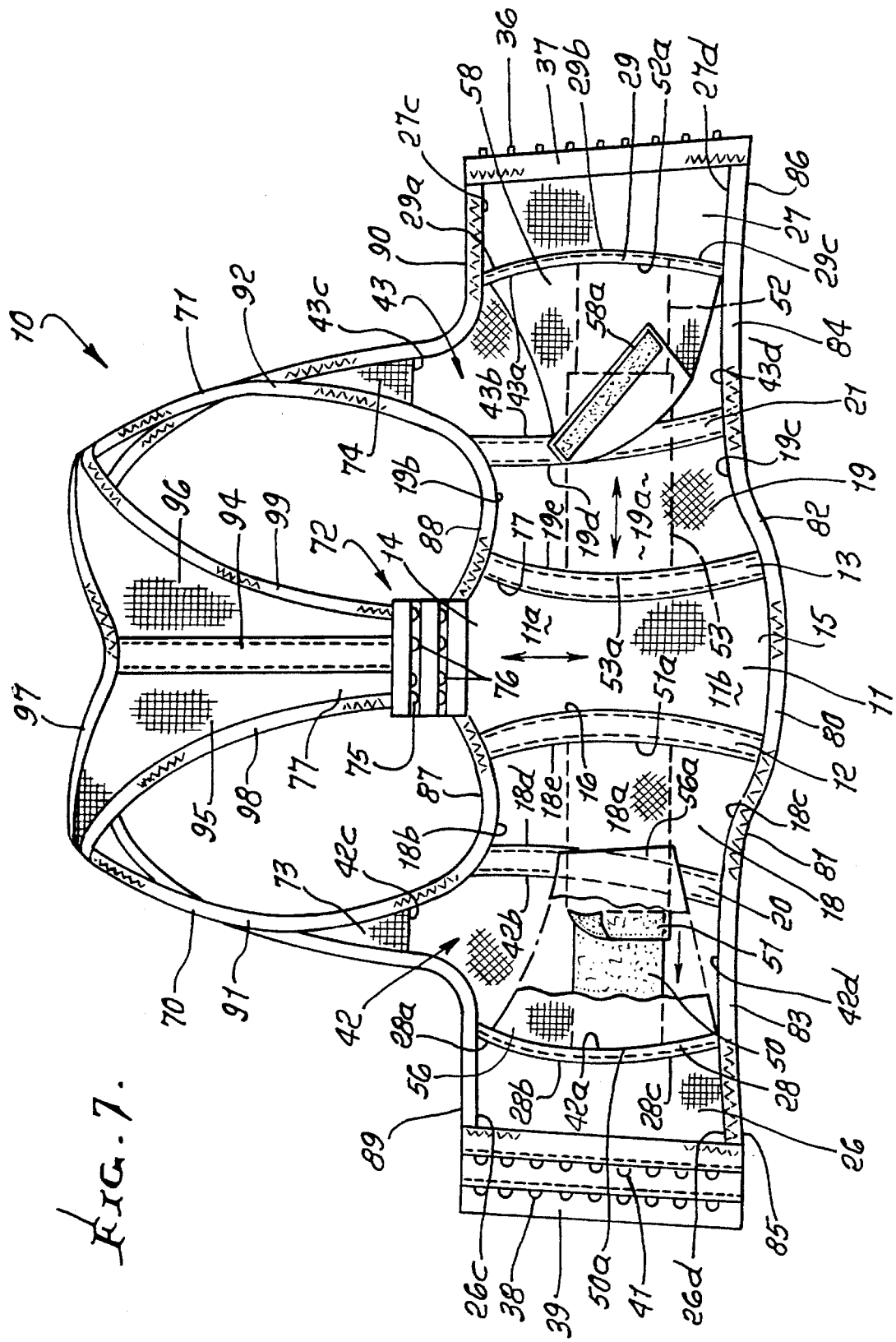
FIG. 7 is a plan view of the FIG. 1 garment when extended on a flat surface.

More specifically, in the illustrated example, the garment 10 has fabric portions as follows:

i) control fabric panel 11 at the garment rear, to face the lower back of the user's torso, at the waist, panel 11 having planar hourglass shape (i.e., downwardly convergent and then divergent at regions 11a and 11b between stay zones 12 and 13, arcuate at 12a, b and c and 13a, b and c. Panel 11 is generally rigid, but may be resiliently yieldably stretchable, to limited vertical extent, but not horizontally stretchable between stays 12 and 13, to "hold in" the user's torso at the back, during forward bending at the waist area, thereby providing lower back support concentrated at the spine area, in part due to the hourglass shape of panel 11. Panel 11 is vertically elongated between upper and lower edges 14 and 15, and between oppositely curved side edges 16 and 17. Panel 11 may consist of polyester strands woven to provide panel rigidity (substantial nonflexibility), but may have limited elasticity to allow vertical stretchability, as referred to.

ii) control fabric panels 18 and 19 at the garment sides, to face the wearer's torso at the waist opposite sides. Panel 18 extends between horizontally spaced stay zones 20 and 12; and like panel 19 extends between horizontally spaced stay zones 21 and 13. Each of panels 18 and 19 is typically wider at its medial extent 18a and 19a, than at its top and bottom edges 18b and 18c, and 19b and 19c. Side edges of the panels 18 and 19, adjacent the stay zones, are designated at 18d and 18e, and 19d and 19e. See FIG. 7. Each of the panels 18 and 19 may consist of the known NYLON fabric "POWER NET" and is resiliently yieldably stretchable, both horizontally and vertically (but preferably more stretchable horizontally than vertically). Two layers of such fabric can be used.

iii) interconnectible control fabric panels 26 and 27 at the garment front, to face and control the wearer's torso at the waist front, i.e., "tummy zone", when interconnected, as will be described. The panels 26 and 27, when connected, have overall planar hourglass shape, i.e., downwardly convergent and then divergent, as seen in FIG. 1, at combined upper regions 26a and 27a; and at combined lower regions 26b and 27b, between curved zones 28 and 29, arcuate at 28a, b and c; and at 29a, b and c. Zones 28 and 29 are connection zones between panel 26 and a panel 42 (described below); and between panel 27 and a panel 43 (described below). The panels 26 and 27 are generally rigid, but may be vertically resiliently yieldable or stretchable, between upper and lower edges 26c and 26d, and between upper and lower edges 27c and 27d, but are not horizontally stretchable, whereby the front of the wearer's waist is not allowed by panels 46 and 27 themselves to expand outwardly, but is allowed to expand vertically, aiding the torso hourglass shape control to be achieved. The panels 26 and 27 interconnection may be advantageously achieved, as by a vertical row of metal hooks 36, on seam binding 37, attached to the edge of panel 27; and at least one vertical row of metal loops 38, on seam bonding 39, attached to the edge of panel 26, as shown, the hooks engaging the respective loops. Another vertical row of loops 41 may be provided on seam binding 39, and spaced adjustably from loops 38, to provide for tightening of the garment, if desired, although the horizontal stretchability of panels, as referred to, allows for size adjustment throughout size range associated with each of the loop rows. Three to four sizes of the garment are contemplated to enable use by females of all waist sizes.

iv) control fabric panels 42 and 43 at transitions between panels 26 and 18, and between panels 27 and 19, are provided to allow tightening and loosening adjustment of the garment about the wearer'8 waist. Panel 42 is attached at horizontally spaced, upright edges 42a and 42b to panels 26 and 18. Like panel 43 is attached at its horizontally spaced upright edges 43a and 43b to panels 27 and 19, as shown. Panels 42 and 43 are each horizontally and vertically resiliently yieldably stretchable to accommodate to the torso at the waist, to allow torso bending; and also to accommodate tightening and loosening adjustment about the waist. Upper and lower edges are indicated at 42c and 42d, and at 43c and 43d.

All panels 18, 42, 14, and 43 are flexible, i.e., bendable, to conform to the wearer's waist. Also, panels 18, 42, 14, and 43 may each consist of two layers of fabric.

CONTROL ADJUSTMENT

As referred to, tightening and loosening of the garment is provided for, while maintaining back support, as well as tummy control, at the torso front, as referred to.

For this purpose, control flaps 50 and 51 are provided to extend horizontally and controllably overlie panels 18 and 42, as shown. Control flaps 52 and 53 are provided to extend horizontally and centrally overlie panels 19 and 43. Flap 50 is end-anchored at 50a near the concave middle of arcuate connection 28; and flap 51 is end-anchored at 51a near the concave middle of arcuate stay zone 12. Thus, when the flaps 50 and 51 are adjustably pulled toward one another and pressed together to fasten together (as by VELCRO or other connection), they pull 28 and 12 over their lengths toward one another, as enhanced or facilitated by the concavities of 28 and 12 toward the flap end connections therewith. The flaps may consist of VELCRO elastic, stretch pile.

Fabric panels 18 and 42 accommodate themselves to this tightening or loosening, by flexing; and stays at zones 12 and 20, although tensioned medially thereof, maintain the shapes of the flexing panels 18 and 42, adjacent thereto, as well as urging them toward or adjacent thereto, as well as urging them toward or against the hourglass-shaped torso, under the influence of the tensioned straps. A protective outer flap 56, also end-anchored at zone 28, overlies connectible overlapping extents of flaps 50 and 51, as is clear from 7. Flap 56 may attach to one or both flaps 50 and 51, as by VELCRO connection; and its free end 56a may be peeled back to give access to the tightening (or loosening) flaps 50 and 51, which are protected by flap 56.

Likewise, flap 52 is end-anchored at 52a, near the concave middle of arcuate connection 29; and flap 53 is end-anchored at 53a, near the concave middle of arcuate stay zone 13. Thus, when the flaps 52 and 53 are adjustably pulled toward one another and pressed together to fasten together (as by VELCRO or other connections), they pull 29 and 13 toward one another, as enhanced or facilitated by the concavities of 29 and 13 toward the flap end connections therewith.

Fabric panels 19 and 43 accommodate themselves to this tightening or loosening, as by flexing. Although tensioned medially thereof, stays at zones 13 and 29 maintain the shapes of the flexing panels 19 and 43 adjacent thereto, as well as urging them toward or adjacent the hourglass-shaped torso, under the influence of the tensioned straps. A protective outer flap 58, also end connected at zone 29, overlies connectible overlapping extents of flaps 52 and 53. Flap 58 may attach to one or both of flaps 52 and 53, as by VELCRO or other type connection; and its free end 58a may be peeled back to give access to flaps 52 and 53 (for tightening or loosening), the latter flaps normally protected by overlying flap 58.

A compact, flat composite of flaps and fabric panels, and stays, is achieved, to protect the lower back (lower lumbar) region, and yet maintain an hourglass shape, flat tummy, and enable rapid adjustability at both sides of the torso or waist.

Stays 60, at stay regions 12, 20, 13, and 21, may take the form as shown in FIG. 8. They are elongated, metallic and flexible. They may take the form of small steel loops 61 that spiral loop-interconnect together, as is known. They are confined in the stay zones, as by jacketing 62, which also serves to interconnect ends of adjacent panels.

FIG. 10 also shows the use of two layers of fabric, as at panel 19. Panel 43 may also be double fabric layered, as referred to. Note that flap 53 extends beneath stay zone 21, and between dual fabric layers at 19.

Shoulder straps 70 and 71 may be provided, as shown, to connect at 72 to upper extent of back panel 11, and to connect to upper extents 73 and 74 of panels 42 and 43. The connection at 72 is shown as vertically adjustable, as via a single horizontal row of hooks 75 on upper extent of panel 11, and two or three vertically spaced, horizontally extending rows of loops 76 on the lower end of a merged rear strap portion 77 of shoulder straps 70 and 71. Vertical adjustability (lengthening or shortening) of the shoulder straps is thereby provided, to accommodate to the size of the wearer. The hooks may be like those at 36, the loops like those at 38. In addition, a nonstretchable, vertical strap 94 extends medially between fabric sections 95 and 96, from connection 72 to upper seam binding 97 extending transversely between 70 and 71.

FIG. 6 shows a form of the garment 10' that lacks shoulder straps, but is otherwise the same as described above.

Figure 11:
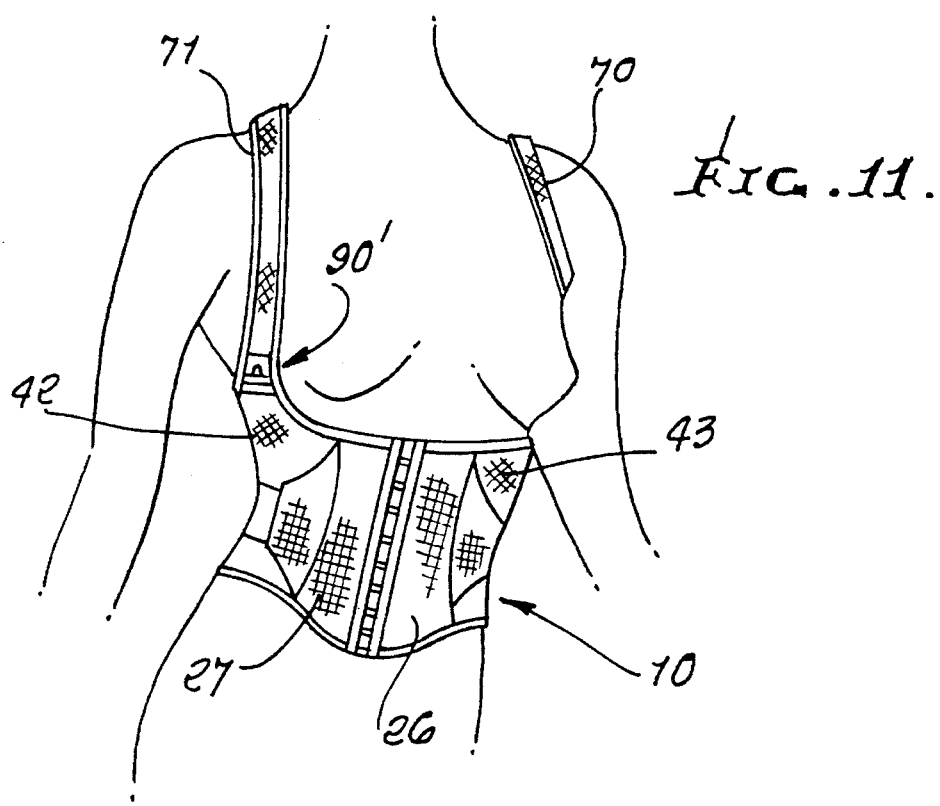
FIG. 11 is a view like FIG. 1 showing a modification.

FIG. 11 shows a shoulder strap adjustable connection at 90 to side panel 42, a similar connection provided to side panel 43.

Figure 12:
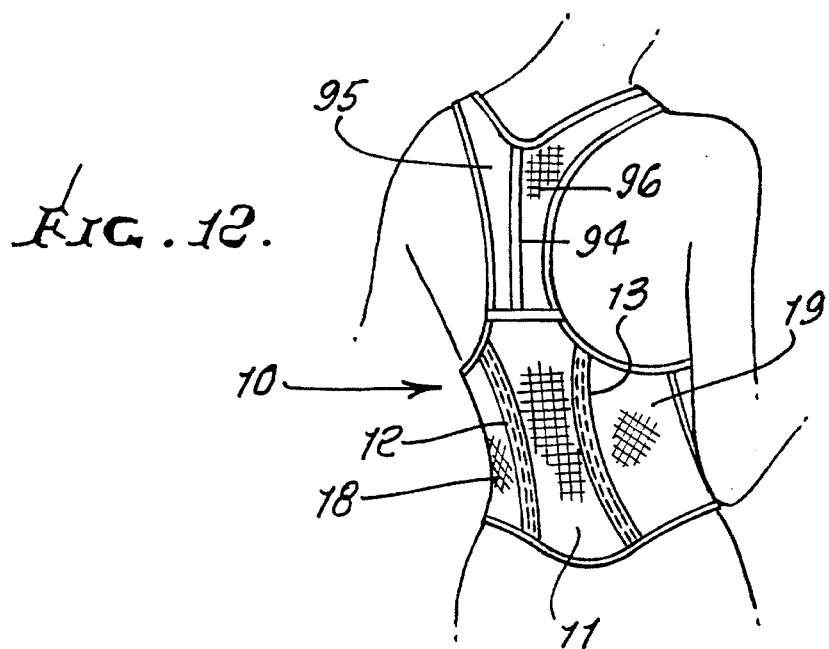
FIG. 12 is a view like FIG. 5 showing a modification.

FIG. 12 shows the back of the FIG. 11 garment, wherein the merged rear strap portion 77 is directly and permanently connected to the garment back panel 11.

Yieldably resiliently stretchable seam binding is also provided along edges of the garment and panels, as indicated at 80–92.

I claim:

1. In a torso-shape controlling, lower back supporting garment, the combination comprising:
   a) said garment having a series of upright fabric panels extending in waist shape controlling relation to torso front, back and sides, said panels including,
   b) a back panel at the garment rear to face the torso back at the waist and characterized as:
      i) vertically elongated and vertically resiliently stretchable, and
      ii) horizontally unstretchable between horizontally spaced edges, there being generally vertically extending stays at said edges,
      iii) said back panel being vertically elongated and having vertical dimension at least twice its maximum horizontal dimension between said edges,
   c) first and second control fabric panels and at the garment sides to face the wearer's torso at the waist opposite sides, and characterized in that:
      i) said first control panel is yieldably resiliently stretchable both horizontally and vertically between horizontally spaced edges, there being generally vertically extending stays at said respective edges of said first control panel,
      ii) said second control panel is generally resiliently stretchable, both horizontally and vertically, between horizontally spaced edges, there being generally vertically extending stays at said respective edges of said second control panel,
      iii) each of said first and second panels having vertical dimension exceeding its maximum horizontal dimension,
   d) first and second front panels at the garment front and that are adjustably interconnected to permit horizontal adjustment, and each characterized as vertically resiliently stretchable, but horizontally unstretchable,
   e) third and fourth control fabric panels at the garment sides to face the wearer's torso at the waist opposite sides, and characterized in that:
      i) said third control panel is yieldably stretchable both horizontally and vertically between horizontally spaced edges, there being generally vertically extending stays at said respective edges of the third control panel,
      ii) said fourth control panel is yieldably stretchable both horizontally and vertically between horizontally spaced edges, there being generally vertically extending stays at said respective edges of the fourth control panel,
      iii) each of said third and fourth control panels having vertical dimension exceeding its maximum horizontal dimension,
   f) and including a first adjustable tightening flap structure connected with said garment to overlie the first and third control fabric panels, and to have tension transmitting connection to said front panel and said back panel, and second adjustable tightening flap structure connected with said garment to overlie the second and fourth control fabric panels, and to have tension transmitting connection to said front panel and said back panel, thereby to permit controllable tightening of the garment about the torso waist.

2. The combination of claim 1 wherein said stays have lengthwise convex curvature to transfer tensioning loading horizontally.

3. The combination of claim 1 wherein said stays are resiliently flexible and metallic.

4. The combination of claim 1 wherein said flap structures include tightening straps associated with said first, second, third, and fourth control panels, said straps having adjustable interconnection to permit controllable tightening of the garment about the torso waist.

5. The combination of claim 4 including a protective overlay strap extending over said tightening strap.

6. The combination of claim 1 including shoulder strap means attached to upper extents of certain of said control panels.

7. The combination of claim 9 wherein said shoulder strap means has adjustable vertical connection to the back panel.

8. The combination of claim 7 wherein said adjustable vertical connection includes multiple interconnectible hooks and loops, one on said back panel, and the other on said shoulder strap means.

9. The combination of claim 6 wherein said shoulder strap means has adjustable vertical connection to certain of said control panels.

10. The combination of claim 1 including adjustable horizontal connection means to adjustably interconnect said front panels.

11. The combination of claim 10 wherein said adjustable horizontal connection means includes rows of hooks and loops, at least one row on one front panel, and at least another row on the other front panel.

12. The combination of claim 1 wherein said back panel is relatively stiff and projects upwardly at the middle of the back.

13. The combination of claim 1 wherein said stays comprise coiled strips of relatively rigid material.

14. The combination of claim 13 wherein said strips have opposite, flat sides throughout their coiled extents.

15. The combination of claim 1 wherein the stays have elongation direction and are bowed in that direction.

* * * * *